United States Patent
Raines

[11] Patent Number: 5,817,455
[45] Date of Patent: Oct. 6, 1998

[54] METHOD FOR IN VITRO INACTIVATION OF RNASE S

[75] Inventor: Ronald T. Raines, Madison, Wis.

[73] Assignee: Novagen, Inc., Madison, Wis.

[21] Appl. No.: 639,806

[22] Filed: Apr. 29, 1996

Related U.S. Application Data

[63] Continuation of Ser. No. 203,536, Mar. 1, 1994, abandoned.

[51] Int. Cl.[6] ........................................... C12Q 1/00
[52] U.S. Cl. ........................... 435/4; 435/23; 435/24
[58] Field of Search ........................ 435/4, 6, 18, 19, 435/23, 24; 436/501

[56] References Cited

U.S. PATENT DOCUMENTS

| | | | |
|---|---|---|---|
| 4,745,054 | 5/1988 | Rabin | 435/6 |
| 5,028,524 | 7/1991 | Fujisawa | 435/5 |
| 5,057,412 | 10/1991 | Rabin | 435/6 |
| 5,563,033 | 10/1996 | Lawrence et al. | 435/6 |

*Primary Examiner*—Ralph Gitomer
*Attorney, Agent, or Firm*—Quarles & Brady

[57] ABSTRACT

A method for inactivating, at a desired stage of an in vitro process, a target enzyme having coupled thereto a biotin molecule, includes adding to a reaction mix an inactivating protein having an affinity for the biotin molecule that is sufficient to inhibit the activity of the target enzyme.

The method is embodied in the ribonuclease activity of the enzyme RNase S, which can be active in a form composed of an S peptide and an S protein, not covalently bound together, which associate to form the catalytic molecule. By adding an affinity moeity to the S peptide, it is possible to a second, inactivating protein having affinity for the affinity moeity to disassociate the S peptide from the S protein, and thereby terminate catalytic activity of RNase S at a desired point in any reaction.

13 Claims, 1 Drawing Sheet

METHOD FOR IN VITRO INACTIVATION OF RNASE S

This is a continuation of application Ser. No. 08/203,536 filed Mar. 1, 1994, now abandoned.

FIELD OF THE INVENTION

The present invention relates to the field of inactivation of an enzyme and relates more particularly to the inactivation of ribonuclease S.

BACKGROUND OF THE INVENTION

When performing a diagnostic or preparative procedure on a biological material in vitro, it may be necessary to perform a series of sequential enzymatic steps. However, it is often undesirable to move to a subsequent step until the enzyme active in an earlier step has been inactivated or removed from the reaction vessel. This limitation is typified in procedures using the ribonuclease (RNase) enzymes, which catalyze the cleavage of single-stranded RNA. RNases are a common tool of the molecular biologist and are among the best characterized of the enzymes. Because RNases are persistent, stable enzymes whose cleavage activity is dramatic and irreversible, it is essential in a diagnostic or preparative technique using RNase at one stage that the cleavage activity be inactivated before, in any subsequent stage, any RNA of interest is exposed to RNase cleavage. While efficient RNase activity can be essential at one stage, RNase activity at a later stage can be fatal.

Diagnostically, RNases are used in RNase Protection Assays (RPA) to destroy single-stranded RNA that has not been protected by hybridization to an RNA probe. Briefly, in an RPA, a radiolabelled RNA probe is mixed with a test RNA population, such as total cellular RNA from an individual, under conditions where complementary segments of the RNA probe and the test RNA will hybridize. RNase is then added to the mixture to destroy unprotected (unhybridized), single-stranded probe and test RNA. When all single-stranded RNA has been destroyed, only short fragments of protected RNA remain that can be analyzed electrophoretically to diagnose genetic lesions in the test RNA. The protected double-stranded RNA fragments are denatured before analysis, to make available the detectable, labeled single stranded RNA probe fragment. In the presence of residual RNase, the labelled single stranded RNA probe would itself be destroyed, undermining the utility of the diagnostic technique.

Preparatively, RNase is used in DNA purification methods to remove extraneous contaminating RNA. Removal of RNA is particularly important when preparing DNA for use in an in vitro transcription or coupled transcription/translation system. In either such system, a DNA construct serves as a template for transcription of large quantities of mRNA, which may be followed by in vitro translation of the mRNA to produce a preparative yield of a desired protein or peptide. Depending upon the goals of the user, either the RNA or protein product may be isolated for analysis or use.

The input DNA template must be free of contaminating RNA so that all transcripts present in the system are genuine, that is, are transcription products of the DNA construct. However, during preparation of template DNA from a host, RNA such as bacterial RNA is typically co-purified. These RNAs must be destroyed before using the purified DNA in an in vitro transcription assay. The most reliable way to do so is to treat the preparation with RNase. Unfortunately, RNase activity is difficult to destroy after it has served its purpose. Yet, it must be destroyed since residual RNase would rapidly hydrolyze any genuine RNA subsequently transcribed from the gene of interest.

The need to remove or inactivate enzymes, including RNases has heretofore been met by subjecting the components of a reaction mix to any of a number of inactivating agents. These agents, which include proteases, heat, acid, base, vanadate-type inhibitors, diethyl pyrocarbonate (DEPC) and denaturants such as urea, guanidinium chloride, or phenol, do not discriminate among the reactants, permanently or reversibly altering the conformation of not only the enzyme which one desires to inactivate, but rather altering the conformation of all protein and nucleic acid biopolymers in the mix.

Denaturation and removal of all the enzymes in a reaction mix may or may not negatively affect a particular analysis or purification, although this limitation is disabling to one who wishes to eliminate the activity of one or a few particular enzyme species from a reaction mix. For example, one may desire to eliminate a ribonuclease activity without inhibiting the activity of other proteins. Or, at a certain stage in a reaction, one may wish to prevent binding of a particular enzyme, but not all enzymes, to a nucleic acid molecule.

A second shortcoming of several known enzyme inactivation methods is that they are laborious. Particularly, phenol extraction of proteins can only be accomplished adequately by several repetitive extraction steps followed by several subsequent extractions and precipitations to remove residual phenol. Even so, particularly stable enzymes, such as RNases, may not be completely inactivated by these steps.

One RNase inhibitor, human placental ribonuclease inhibitor, has been shown to bind tightly to bovine pancreatic ribonuclease A ($K_i$=4.4×10$^{-14}$ M), although when the bound complex is diluted or placed in an oxidizing environment such as air, active RNase A is re-released, its activity having only been temporarily eliminated. However, it has not heretofore been possible to selectively target particular enzymes for permanent inactivation.

SUMMARY OF THE INVENTION

Figure 1:
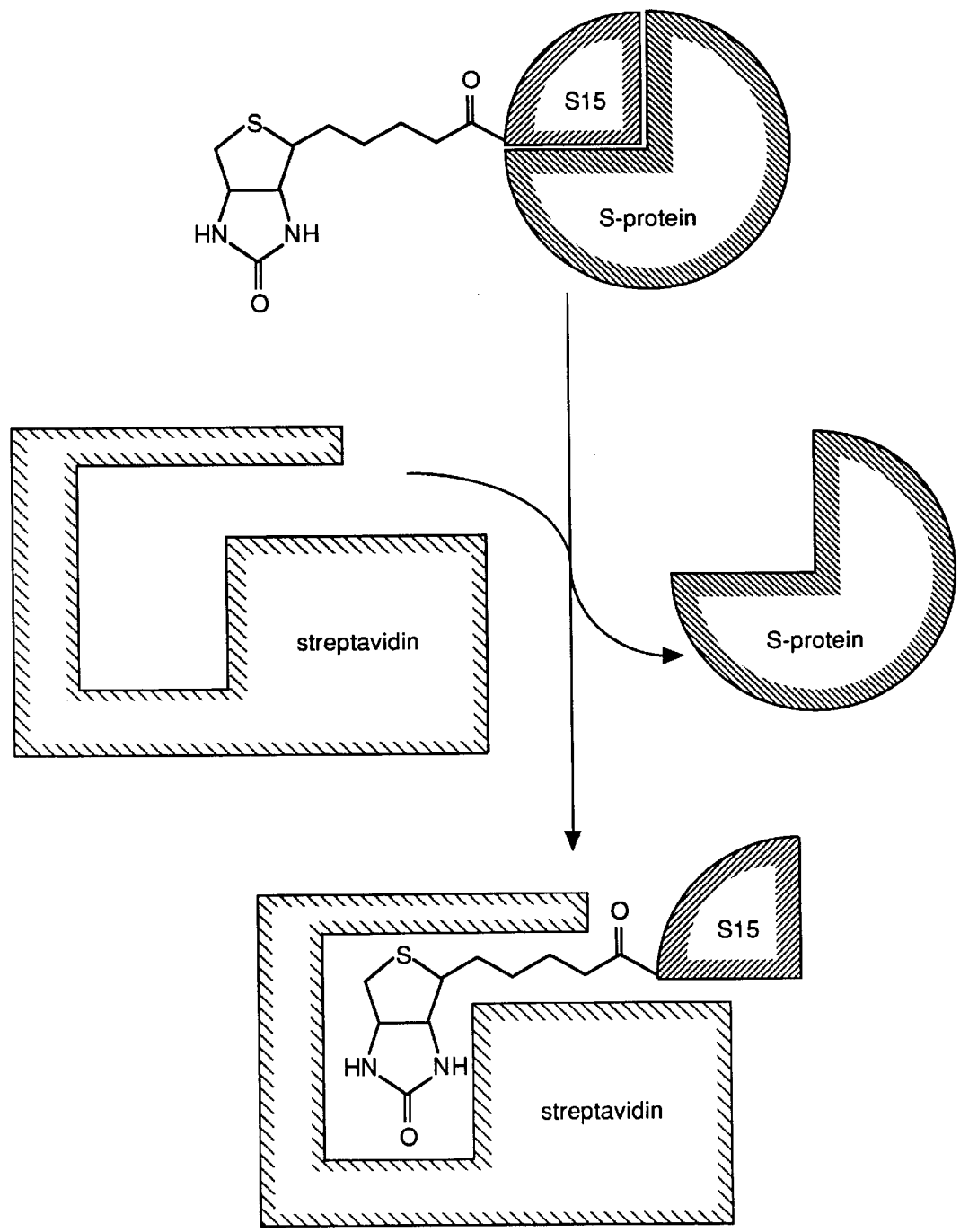
FIG. 1 is a highly stylized schematic illustration of the principle of operation of the present invention.

The present invention is summarized in that in a diagnostic or preparative reaction mix, an enzyme provided with a biotin molecule coupled thereto may be inactivated by adding to the mix an inactivating protein having a substantial affinity for the coupled biotin, where the affinity of the inactivating protein for the biotin-coupled enzyme is sufficiently great so as to disassociate or alter the enzyme, thereby inhibiting the activity of the enzyme.

The invention is directed to a method for inhibiting any activity of an enzyme, including, but not limited to, enzymatic or catalytic activity. The activity inhibited by the added protein will vary according to the native function or functions of the enzyme affected. In one aspect, the invention includes a method for inactivating a monomeric protein, by altering the conformation of the protein or by blocking a functional site on the protein. In a second aspect, the invention includes a method for inactivating a multimeric protein, by either of the previous techniques or by tightly binding to one of the monomers so as to prevent, by steric hindrance, that monomer from joining with any others.

It is an object of the present invention to provide a mechanism-directed method for selectively inactivating a target enzyme.

It is a feature of the present invention that the target enzyme has coupled thereto, on a biologically inactive amino acid residue, a biotin molecule which has a strong affinity for a blocking protein.

It is another feature of the present invention that the affinity of the inactivating protein for the biotin molecule coupled to target enzyme affects the structure or conformation of the target enzyme, rendering it inactive.

It is an advantage of the present invention that the target enzyme is rendered inactive even without removal of the target enzyme from the reaction mix.

It is a further advantage of the present invention that, in a target enzyme having multiple subunits, the sequestering of a subunit needed for activity prevents the enzyme from being active.

Other objects, features and advantages of the present invention will become apparent upon consideration of the following specification.

DETAILED DESCRIPTION OF THE INVENTION

In accordance with the present invention, the target enzyme for use in the present invention is modified to include an affinity moiety, such as biotin. After the desired catalytic activity of the enzyme has been achieved, the inactivating protein is added to the reaction. The inactivating enzyme is selected to have particularly strong affinity for the affinity moiety. The strong binding of the inactivating protein to the affinity moiety can pull apart or disrupt the target enzyme so as to disrupt its function. This disruption is particularly effective with enzymes which are dimeric or multimeric, where the affinity of the inactivating protein for the affinity moiety is strong and the inactivating protein is of a size and shape so as to effectively prevent any re-assembly of the active multimeric form of the enzyme.

Inactivation is envisioned to include the inhibition of any ascertainable activity of interest of the target enzyme. Every target activity need not be inhibited by the inactivation protein. Rather, inactivation of any target activity which the user desires to eliminate from a reaction is sufficient to accomplish inactivation within the scope of the present invention.

The inactivating protein inactivates the target enzyme upon interaction with an affinity moiety, preferably biotin, by sufficiently altering the secondary or tertiary structure of the target material to destroy an active site, or by sterically interfering with an active site, or by physically restraining the biotin-coupled portion of the target from forming a functional, active enzyme. An active site may be, for example, involved in facilitating combinations of monomers or in promoting enzymatic activity.

A target enzyme within the scope of the present invention may be any enzyme having an in vitro enzymatic activity which a user desires to exploit and then to eliminate. The target may be, for example, a monomeric or multimeric protein, peptide, hormone or any other bioactive polymer formed, in whole or in part, of amino acids. In this patent application, the terms enzyme, protein, peptide, and hormone may be used interchangeably to refer to the target enzyme. References to monomeric proteins refer to proteins in which biological activity resides in a single subunit. Multimeric proteins are active when two or more subunits assume an appropriate conformation and spatial relationship to one another to form an active site. In a monomeric protein, intrachain non-covalent forces between and among amino acid residues interact to form three dimensional structures such as active sites and binding sites. In a multimeric protein, the ability of the various monomers to interact to form a functional protein depends upon both intrachain and interchain non-covalent forces. The multimeric target protein may be composed of identical or heterologous monomers. A dissociation constant, $K_d$, measures the strength of attractive non-covalent forces between monomers in a multimeric protein. When comparing the attraction between pairs of molecules, a smaller $K_d$ signifies a stronger attraction.

The target enzyme may be obtained in any way that one would otherwise obtain a purified protein for use in an in vitro reaction. For example, a target protein may be purified from a natural plant, animal, bacterial or viral source, or may be produced in vivo or in vitro as a product of a genetically engineered recombinant DNA molecule using techniques known to the art, or may be chemically synthesized.

To become a true target protein, in the sense of being a target for the inactivating protein, the protein having the desired activity is then biotinylated. The art is generally cognizant of methods for biotinylating proteins. Various biotin derivatives are commercially available for targeting coupling to particular reactive groups on the target. Preferably, the biotinylated target is a semi-synthetic enzyme. A semi-synthetic enzyme is an enzyme purified from a biological system which is subsequently chemically modified. With existing technology, it is easiest to attach biotin to the nitrogen, oxygen, and sulfur atoms of natural amino acid residues. For example, an N-hydroxysuccinimide ester of biotin (available as ImmunoPure NHS-Biotin from Pierce) may be reacted with a primary amine to link the biotin molecule to the nitrogen by amide linkage.

The biotinylated amino group may be coupled to any amino acid in the target protein, although it is preferred that the biotin be coupled so as to not interfere with a desired activity of the target enzyme. Yet, at the same time, it is also preferred that the biotin be coupled to the target in such a way that introduction of the inactivating protein will inhibit the target protein activity of interest.

Since peptides are generally synthesized from the C-terminus to the N-terminus, the activated carboxylic acid group of NHS-biotin behaves like the activated carboxylic acid group of an amino acid during peptide synthesis. The biotin becomes attached to the peptide by an amide bond between the carboxylic acid group of biotin and the amino group at the N-terminus of the peptide. Unlike an amino acid, which has both an amino group and a carboxylic acid group, biotin does not have an amino group. Thus, after biotin is attached to the N-terminus of a peptide, the peptide chain can no longer be extended. Although biotin is preferably coupled to the amino-terminus of a peptide, it is believed that any residue other than those that have been shown to form part of an active site can equally well be chosen for biotinylation. In such cases, the biotin molecule would be attached to a residue other than an alpha amino group. It is specifically envisioned that future developments in peptide chemistry may facilitate biotinylation of other atoms in an enzyme molecule.

It is not necessary that the biotin molecule be directly coupled to the target enzyme. A spacer may be inserted therebetween without necessarily affecting the inactivation of the target.

Methods for preparative isolation of biotin-coupled molecules is well known. In a preferred method, the crude preparation is passed over a reverse phase chromatography column. Alternative purification steps commonly used in the art of protein purification may also be employed. These include affinity chromatography to an avidin-coupled matrix. Biotin-coupled material that is non-covalently retained in the affinity column may be released and recovered by passing competitive quantities of free biotin through the column.

The inactivating protein may be any protein having a strong affinity for biotin. Preferably, the inactivating protein is avidin or streptavidin. Both are readily available commercially. The strong affinity of avidin and streptavidin for biotin is known. The affinity is typically exploited in processes for labelling proteins, nucleic acid and other molecules to facilitate their detection by bringing together a biotin labelled probe and an avidin or streptavidin-labelled detectable molecule such as a color indicator. Avidin is a 68 kDa glycoprotein composed of four identical subunits, each of which non-covalently binds a single biotin molecule. The biotin-avidin complex is remarkably stable, having a dissociation constant of $10^{-15}$M. Streptavidin is a tetrameric protein of molecular weight 60 kDa isolated from Streptomyces avidinii. Streptavidin is functionally similar to avidin and may be used interchangeably therewith to form non-covalent complexes with biotin.

In the present invention, the affinity between biotin and the inactivating protein, such as avidin or streptavidin, is exploited to disrupt the secondary or tertiary structure of a target enzyme molecule. Addition of the inactivating protein, uncoupled to another molecule, attracts the biotin molecule coupled to the target enzyme. In so doing, the target enzyme is distorted to the point of inactivity.

In a preferred embodiment, the distortion is a virtually irreversible separation of the subunits of a multimeric enzyme which results from the strong non-covalent attraction between biotin and the inactivating protein. Since the attraction between the two is stronger than the non-covalent attraction among the target enzyme subunits, the biotin-coupled subunit is, practically speaking, sequestered away from the other subunits of target enzyme. The target enzyme lacks an obligate subunit, and is, therefore, rendered inactive. It is believed that the inactivation method disclosed herein can inactivate any target enzyme in which the affinity of the inactivating protein for the biotin is substantially greater than the affinity of the biotin-coupled monomer for the rest of the target enzyme.

The invention is not intended to be limited to multimeric proteins, however. The same inactivation process is believed to be able to inactivate single chain monomeric enzyme as well, albeit in a somewhat different way. Upon addition of an inactivating protein to a reaction mix containing a monomeric target enzyme, the strong and virtually irreversible affinity for the coupled biotin draws the inactivating protein to the target enzyme and in so doing distorts the target enzyme, either by changing its three dimensional structure or by sterically interfering with an active site. In either case, the net result is inactivation of the target.

When designing strategy for inactivating a monomeric target enzyme, it is advantageous to couple the biotin to an amino acid that is in relatively close proximity to the active site. In contrast, a biotin molecule coupled at a great distance from the active site of a single chain target enzyme might have little or no effect on the activity, upon addition of the inactivating protein.

The preferred embodiment of the invention is demonstrated in the following preferred example by a method for inactivating a semi-synthetic RNase S enzyme. RNase S, is a derivative and functional equivalent of bovine pancreatic RNase A. Limited digestion of RNase A by the protease subtilisin produce two cleavage products, S-peptide (residues 1–20 of RNase A) and S-protein (residues 21–124). Both S-peptide and S-protein, as well as derivatives thereof, are commercially available. Although neither of these two fragments alone is an active RNase, S-peptide binds S-protein to form RNase S, which retains the full catalytic activity of RNase A. The S-peptide and S-protein have a dissociation constant of $10^{-9}$ M. Although this is considered to be a strong association, it is six orders of magnitude weaker than the $K_d$ of biotin and streptavidin.

It is thus intended that in a biochemical process that requires RNase activity, that free S-peptide and S-protein be used. Under normal nucleotide-handling conditions, the two fragments function as monomers which spontaneously bind to form the heterodimer RNase S. The biotin affinity moiety is preferably attached to the S-peptide, and can conveniently be attached to the amino group of the carboxyl terminus lysine residue. This is illustrated in schematic fashion in FIG. 1.

After the desired catalysis using the RNase S is performed, streptavidin is added to the reaction mixture. The binding of the biotin for strepavidin is highly favored over the binding of the S-peptide to the S-protein. The resulting re-association is also illustrated schematically in FIG. 1.

With the streptavidin bound to it, the S-peptide can no longer bind to the S-protein. The large size of the strepavidin molecule sterically hinders re-association and effectively prevents the sites of interaction between the S-peptide and the S-protein from even becoming close to each other. In essence, the simple addition of strepavidin to the reaction mixture entirely inhibits the RNase activity.

The inactivation method of the present invention may be advantageously applied in a ribonuclease protection assay in which a test population of RNA is mixed with a sequence-specific probe RNA under conditions of time and concentration that permit non-covalent hybridization between complementary portions of the probe RNA and the test RNA. Then, the unhybridized single stranded RNA is destroyed by adding a ribonuclease that may subsequently be inactivated using the method of the present invention. Preferably, the RNase is RNase S formed of an S-protein and an S-peptide, the S-peptide being covalently coupled to a biotin molecule. The RNase is added at a sufficient concentration and temperature, and for a sufficient length of time, to degrade the single-stranded RNA.

After the residual RNA has been destroyed, the biotin-coupled RNase S is inactivated by adding an effective, or preferably excess, amount of an inactivating protein, such as avidin or streptavidin to the reaction mixture.

The following example is intended to be purely exemplary of the method of the present invention.

EXAMPLE

A truncated S-peptide formed from the first 15 residues of the S-peptide, referred to as S15, which binds equally well to S-protein as does intact S-peptide, was used in all aspects of the disclosed embodiment. S-peptide is available from Sigma Chemical Co. S15 is not commercially available but may be synthesized in vitro using techniques known to the art. The amino acid sequence of the S15 truncated S-peptide is known to the art, and is presented herein as SEQ ID NO:1.

To form a target RNase S enzyme, NHS-biotin (Pierce, product number 20217 G) was chemically coupled to the amino-terminal lysine of the S15 peptide to yield a functional biotinylated S-peptide derivative referred to as bS15, the amino acid portion of which was identical to S15 of SEQ ID NO:1. Biotinylation of the alpha-amino group of lysine in position 1 of the S15 molecule was accomplished using standard methods (Bodanszky, M., "Peptide Chemistry," Springer-verlag, New York, 1988) and reagents, according to the instructions provided by the supplier of NHS-biotin. The biotinylated S15 peptide (bSl5) was purified by affinity chromatography on avadin-agarose followed by C18 reverse phase high performance liquid chromatography.

Authentic, unbiotinylated S15 peptide was synthesized by Operon Technologies and was used without further purification. S-protein was purchased from Sigma Chemical Co. Contaminating RNase A and RNase S were removed by affinity chromatography on AMP-agarose. Streptavidin, used in this example as the inactivating protein, was purchased from Pierce.

Ribonuclease S activity was measured in terms of degradation of yeast polymeric RNA. Degradation was monitored as an increase in absorbance at 255 nm of the reaction cocktail. The reaction cocktail included 50 mM imidazole-.HCl buffer, pH 7.0, 0.1 M NaCl, and 75 ug/mL yeast RNA, in a volume of 800 uL. The change in absorbance was monitored at 25° C. for 2 minutes following the consecutive addition of S-protein (50 ng), bS15 (approx. 5 μg), streptavidin (10 μg), and authentic S15 (5 μg).

Table 1 reports the results of these assays. For comparison, the degradative activity in a reaction mix containing S-protein (50 ng) plus S15 (10 μg) is defined to be 100%. Sequestration of the available biotinylated S15 from its S-protein counterpart by streptavidin was shown to be sufficient to inactivate RNase S. Addition of S15 as the last step of the test demonstrated that RNase S activity could be reconstituted by making available free, unsequestered S15. The initial velocity of each reaction was determined from the initial slope of a plot of absorbance v. time.

TABLE 1

| Reagent | Activity |
| --- | --- |
| S-protein + S15 | 100% |
| S-protein | <0.01% |
| +bS15 | 64% |
| +streptavidin | <0.01% |
| +S15 | 40% |

It is to be understood that the present invention is not limited to the particular embodiments disclosed in this application, but embraces all such modified forms thereof as come within the scope of the following claims.

I claim:

1. A method for conducting an in vitro reaction catalyzed by RNase S, the method comprising:

providing an RNase S enzyme formed of an S-protein and S-peptide, the S-protein and the S-peptide not being covalently bound to each other, one of the S-protein and the S-peptide having covalently bound to it an affinity moiety which has an affinity to an inactivating protein, the affinity of the affinity moiety to the inactivating protein exceeding the affinity of the S-protein for the S-peptide;

combining the RNase S enzyme with substrates on which the RNase S can act catalytically, in a reaction mix;

permitting the RNase S enzyme to react on the substrates in the reaction mix until such time as a desired amount of catalytic activity has occurred; and adding to the reaction mix an amount of the inactivating protein having a binding affinity to the moiety so as to disassociate the S-peptide from the S-protein, to inactivate the catalytic activity of the RNase S enzyme in the reaction mix.

2. A method as claimed in claim 1, wherein the in vitro reaction is a purification of DNA free of ribonuclease activity.

3. A method as claimed in claim 1 wherein the affinity moiety is biotin.

4. A method as claimed in claim 3, wherein the inactivating protein is avidin.

5. A method as claimed in claim 3, wherein the inactivating protein is streptavidin.

6. A method as claimed in claim 1, wherein the S-peptide is truncated at its carboxyl end.

7. A method as claimed in claim 1, wherein the structure of the S-peptide is biotin-Lys-Glu-Thr-Ala-Ala-Ala-Lys-Phe-Glu-Arg-Gln-His-Met-Asp-Ser.

8. A method as claimed in claim 1, wherein the in vitro reaction is a ribonuclease protection assay.

9. A method for inactivating the ribonuclease activity of RNase S in an in vitro reaction mix, the RNase S formed from an S-peptide and an S-protein having an affinity for each other, the method comprising the steps of:

coupling a biotin molecule to the S-peptide of the RNase S by covalent linkage thus forming a biotin-coupled RNase S which retains ribonuclease activity;

adding the biotin-coupled RNase S into an in vitro reaction mix;

permitting the biotin-coupled RNase S to perform ribonuclease activity until such time as a desired amount of ribonuclease activity has occurred; and adding to the reaction mix an amount of an inactivating protein having a sufficiently high affinity for the biotin that a non-covalent interaction between the inactivating protein and the biotin in the biotin-coupled RNase S inactivates the ribonuclease activity of the RNase S.

10. A method as claimed in claim 9 wherein the inactivating protein is streptavidin.

11. A method as claimed in claim 9 wherein the inactivating protein is avidin.

12. A method as claimed in claim 9 wherein the inactivating protein has an affinity for the biotin that is substantially higher than the affinity of the S-peptide for the S-protein, such that the ability of the S-peptide and the S-protein to combine to form the RNase S is reduced.

13. A method as claimed in claim 9 wherein the S-peptide is truncated at its carboxyl terminus and is biotinylated at its amino terminus.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 15 amino acids
( B ) TYPE: amino acid
( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: N-terminal ( x i ) SEQUENCE DESCRIPTION: SEQ ID NO:1:

```
Lys  Glu  Thr  Ala  Ala  Ala  Lys  Phe  Glu  Arg  Gln  His  Met  Asp  Ser
1                  5                        10                       15
```